United States Patent [19]

Sandhaus

[11] Patent Number: 4,807,644

[45] Date of Patent: Feb. 28, 1989

[54] TEMPERATURE-REGULATING SURGICAL DRAPE

[75] Inventor: Jeffrey J. Sandhaus, Astoria, N.Y.

[73] Assignee: Vastech Medical Products Inc., New Brunswick, N.J.

[21] Appl. No.: 13,773

[22] Filed: Feb. 12, 1987

[51] Int. Cl.⁴ .............................................. A61F 13/00
[52] U.S. Cl. ..................................... 128/849; 128/853
[58] Field of Search ............... 128/132 D, 132 R, 402, 128/403, 134, 399; 604/113, 114; 219/212, 528

[56] References Cited

U.S. PATENT DOCUMENTS

| | | | |
|---|---|---|---|
| 3,175,558 | 3/1965 | Caillouette | 128/403 |
| 3,763,857 | 10/1973 | Schrading et al. | 128/132 D |
| 3,951,127 | 4/1976 | Watson et al. | 128/403 X |
| 4,316,456 | 2/1982 | Stoneback | 128/132 D |
| 4,413,624 | 11/1983 | Snow | 128/402 X |
| 4,573,447 | 3/1986 | Thrash et al. | 128/403 X |

Primary Examiner—Robert A. Hafer
Assistant Examiner—Kevin G. Rooney
Attorney, Agent, or Firm—Lerner, David, Littenberg, Krumholz & Mentlik

[57] ABSTRACT

Temperature regulating surgical drapes are disclosed for use in conducting surgical procedures including a drape body with an opening adapted to expose only the specific body portion during surgery and including heat generating or cooling elements affixed to the drape at a localized position surrounding the opening to maintain that body portion at a specified temperature during surgery.

28 Claims, 2 Drawing Sheets

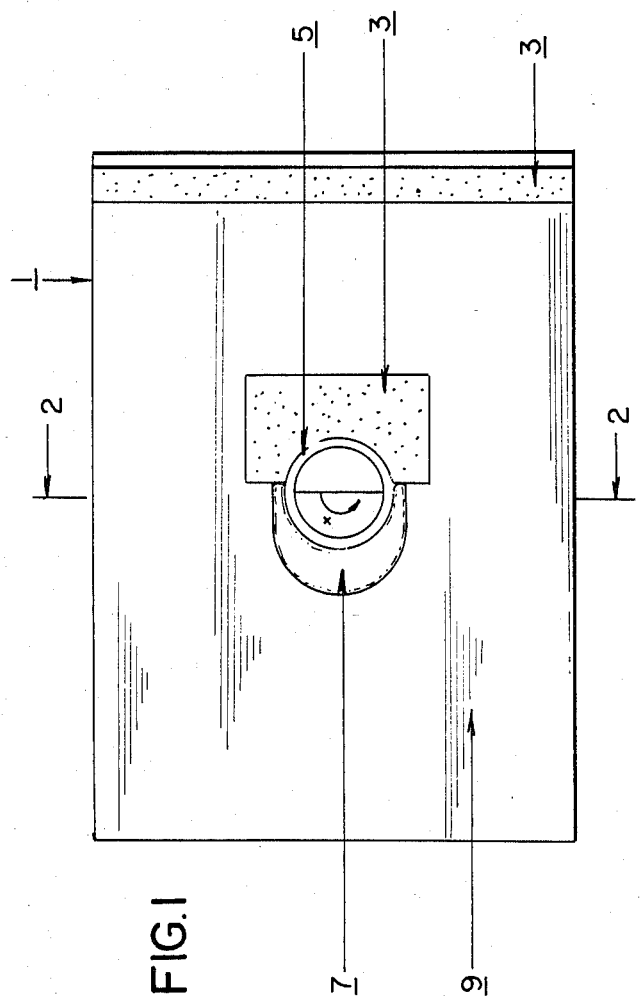
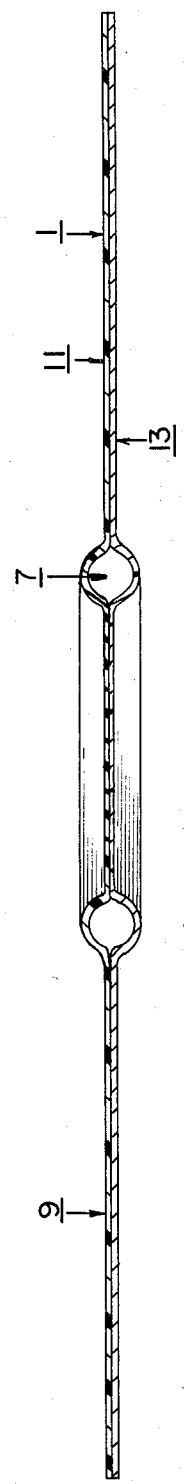
FIG.1
FIG.2

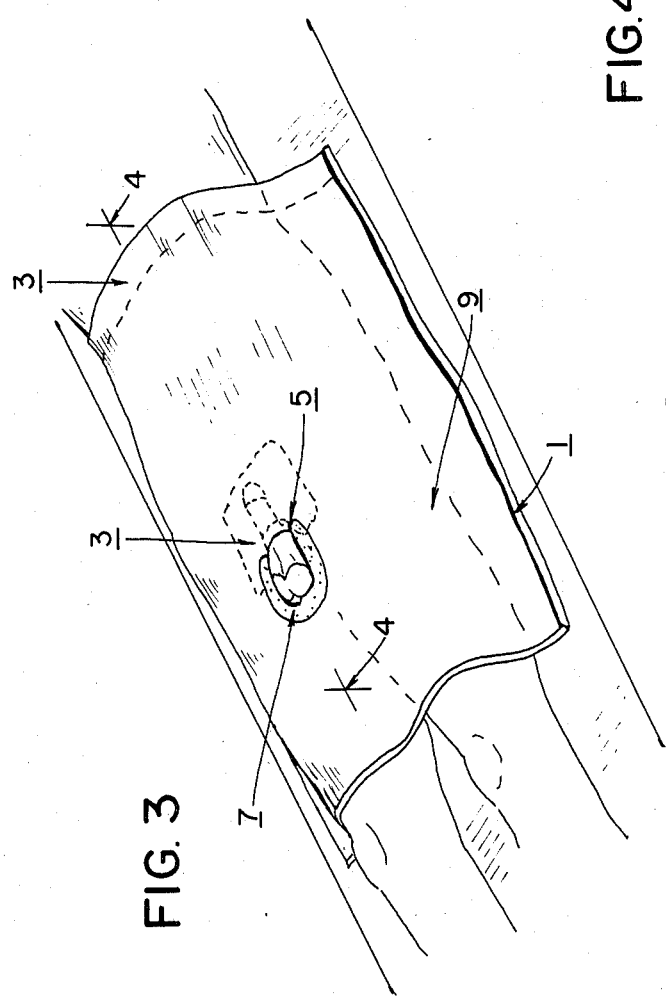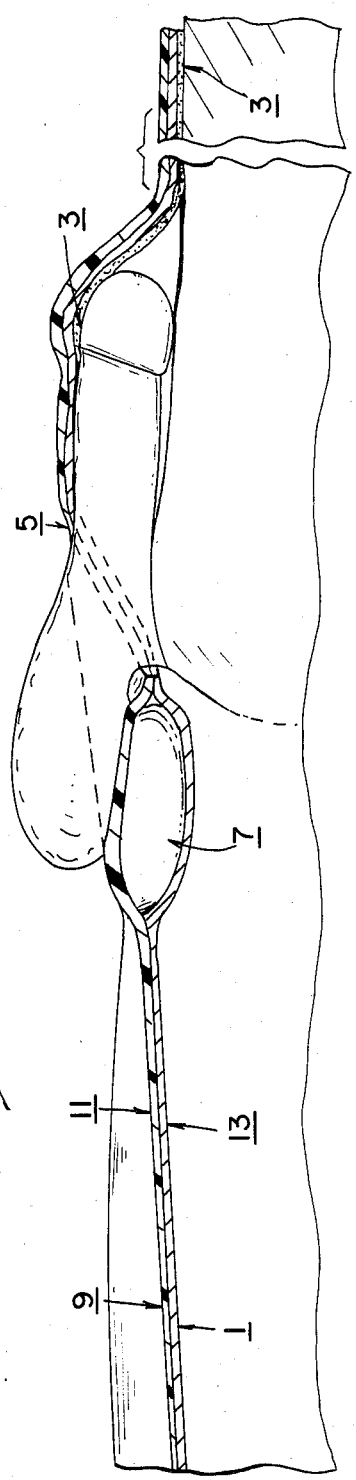

TEMPERATURE-REGULATING SURGICAL DRAPE

FIELD OF THE INVENTION

This invention relates generally to fenestrated surgical drapes, temperature-regulating surgical devices, and more specifically, to self-warming or self-cooling surgical drapes for use in scrotal surgery.

BACKGROUND OF THE INVENTION

Most surgical procedures require the use of fenestrated drapes which allow the surge ion access to the appropriate body region while simultaneously covering the rest of the body. The use of surgical drapes is not confined to humans. They are frequently used in animal surgery whenever it is desirable to cover all of the body save the operating field. Such drapes today are usually disposable and water repellant. They can be attached to the body by adhesive to prevent sliding during surgery. Drapes of this sort are usually best-suited to use on relatively flat, smooth portions of the body such as the abdomen.

In performing vasectomy procedures the surge ion operates on the patient's scrotum. Such procedures present special surgical problems. The male reproductive organs' shapes are not ones to which surgical drapes readily conform. The scrotum tends to thicken and contract when cooled during exposure. This causes the testes and sperm ducts to move upward toward the groin, making surgery in this region difficult. Scrotal surgery is normally performed with the patient lying on his back and his penis placed against his abdomen with its lower surface facing upward. This is not a stable position and the penis frequently enters into the surgical field.

Fenestrated surgical drapes are manufactured with openings which allow access to the surgical field. They can be produced in a variety of forms and with a variety of sizes and shapes of surgical openings. Normally the surgical drape is placed above the surgical zone. When operating on irregularly shaped regions it may be advantageous to position the drape in a different manner. It is suggested that when surgery is performed in the scrotal region the scrotum be passed through a hole in the drape and placed above the drape. This orientation has two benefits; it isolates the scrotum from the body, and it locates the penis under the drape so as to keep if from intruding into the field of surgery.

The scrotum contracts or relaxes in reaction to changes in temperature. When cooled, it contracts and its surface thickens, pulling the testes and sperm ducts upward toward the body. Such changes make surgery more difficult and so it is desirable to keep the scrotum warm to encourage the desirable relaxation response. Presently, surgical aids for maintaining a desired temperature include heat lamps, electrical heating pads, and sterile wet toweling. All require the use of expensive reuseable equipment, which must be sterilized before later use and which can clutter or obstruct the surgical field.

Pouchlike heating or cooling devices containing separated chemical reactants, which only change temperature when manipulated so as to mix those reactants by rupturing at least one internal pouch are admittedly well-known in the art. See, for example: U.S. Pat. Nos. 4,080,953 (Mitchell); 3,854,156 (Williams); and 3,175,558 (Cailouette). Similarly, fenestrated surgical drapes are well-known; see U.S. Pat. No. 4,316,456 (Stoneback). Williams, the closest to theses patents to the instant invention, teaches only the use of a chemically-activated temperature regulating device in a combination mattress and blanket for transporting infants. It does not contemplate use in surgery. The now-expired Cailouette patent teaches the use of a chemically-activated temperature-regulating pack surrounded by a disposable outer cover, but does not contemplate use in surgery. The present invention successfully combines the temperature-control function of the already-known thermal pouches with the field-isolating function of surgical drapes in a low-cost, disposable structure, while simultaneously facilitating unimpeded access to the surgical field.

The present invention solves both the problems of scrotal contraction and intrusion of the penis into the surgical field.

OBJECTS AND STATEMENT OF THE INVENTION

It is therefore an object of the present invention to provide a surgical drape which allows maintenance of the surgical field within a preselected temperature range.

It is another object of the present invention to provide a surgical drape which will permit maintenance of the scrotum within a preselected temperature range.

It is a further object of the present invention to provide a surgical drape which, while isolating and exposing the scrotum, serves to keep the penis from intruding into the surgical field.

In one advantageous embodiment of an apparatus employing the instant invention, the temperature control and restraining functions are achieved by providing the following. A multilayered surgical drape with a centrally located opening of size slightly larger than the scrotum is employed. A strip of suitable adhesive runs along a portion of the perimeter of the lower surface of the drape. Another strip may be located adjacent to the edge of the drape's central opening. Both of these strips can be covered with plastic sheeting until use.

A thermal bag is fixably secured to the drape in such an orientation as to place its main portion nearest the patient's feet. The thermal bag lies underneath the patient's scrotum. The scrotum passes through the drape's opening and rests above the portion of the drape containing the thermal bag. The penis is kept out of surgical field (its top surface is held against the patient's abdomen,) and is medially located above the body and beneath the drape. The drape is further restrained by the aforementioned adhesive strips found on its lower surface.

The thermal bag attached to the drape is a flexible, leak-proof sack containing a primary reactant and a second smaller internal bag. The smaller internal bag is constructed such that vigorous bending or squeezing of the outer bag will cause the smaller internal bag to rupture. The internal bag contains a secondary reactant which, upon contact with the primary reactant disposed throughout the external bag, experiences either an exothermic or endothermic reaction which changes the temperature of the assembly. The primary and secondary reactants can be selected to cause the surgical field to achieve a temperature within a predetermined range. The aforementioned quality whereby vigorous bending or squeezing ruptures the internal bag but not the external bag is called "manipulable rupturability." A manipulably rupturable bag must be constructed to protect against accidental rupture if dropped or mishandled, while not requiring undue effort to deliberately rupture the bag.

In another advantageous embodiment the drape's opening is constructed so that its perimeter elastically conforms to the portion of the scrotum passing through it. This facilitates isolating the surgical field.

In actual operation the drape is removed from its sterile container and the bag is manipulated to break the internal bag, mixing the reactants and as a result of either an endothermic or exothermic reaction changing the bag temperature. The plastic sheeting covering the adhesive strips is removed and the fresh adhesive exposed. The drape is placed on the patient's torso; the penis is held under the drape against midline of the abdomen. The drape should be oriented so that the median of the bag is closest to the patient's legs. The scrotum is passed through the opening and placed atop the thermal bag.

Two advantages pertain to users of this invention. First, the scrotum can be kept warm by choosing reactants which, when combined, release heat. This will cause the scrotum to relax and descend, facilitating access to the organs therein.

Second, the penis will be kept from shifting into the operating field because it is held beneath the surgical drape, itself held immobile by the adhesive strips on its lower side.

The foregoing objects, features and advantages of the present invention will become apparent from the following description of preferred embodiment in connection with the accompanying drawings.

BRIEF DESCRIPTION OF THE DRAWINGS

FIG. 1 is a top elevational view of one embodiment of the present invention.

FIG. 2 is a cross-sectional view of one embodiment of the present invention as seen along line 2—2 in FIG. 1.

FIG. 3 is a perspective view showing one embodiment of the present invention as used in surgery.

FIG. 4 is a cross-sectional view as seen along line 4—4 in FIG. 3.

DETAILED DESCRIPTION OF PREFERRED EMBODIMENT

Referring now to the drawings and, in particular, to FIGS. 1-4, there is depicted one embodiment of an apparatus in accordance with the present invention.

A surgical drape assembly 1, having an opening 5, is located in the drape surface 9. Adhesive strips 3 are located on a portion of the underside of the drape surface 9. A thermal bag 7 containing a temperature regulating means which is activated by selective manipulation of the thermal bag 7 is fixed about opening 5. The thermal bag 7 has the approximate shape of a semiannular section subtending an angle x about the center of a toroid describing an annulus about said opening 5, said angle x being between 0 and 360 degrees. This shape is merely one of a myriad of other possible forms which will work equally well, such as discs, oblongs or polygons, either enclosing or adjacent to the opening 5. The thermal bag 7 is fixed between an upper drape surface 11 and a lower drape surface 13 as shown in FIG. 3. The thermal bag can also, if desired, be attached only to a surface of the drape 9.

The surgical drape assembly 1 is aligned so that the patient's scrotum passes through the opening 5 and rests upon the portion of the assembly containing the thermal bag 7. The patient's penis rests underneath the drape assembly 1 and is securely held by contact with a portion of an adhesive strip 3. Another adhesive strip 3 secures the drape assembly 1 to the patient's body. The scrotum, passing through the opening 5 rests on the upper drape surface 11 atop the thermal bag 7. The bag is fixably held between the upper drape surface 11 and th lower drape surface 13. One adhesive strip 3 attaches the penis to the lower drape surface 13 and another adhesive strip 3 attaches the lower drape surface to the patient's body.

The invention is employed using the following procedure: The thermal bag 7 is specifically manipulated so as to activate its termperature-regulating means. Such temperature-regulating bags are well known and often bag ("first bag") contains a primary reactant and an inner, rupturable bag ("second bag,") contains a secondary reactant. The second bag breaks only after specific manipulation of the first bag. The reactants then mix and chemically combine in the still-intact first bag. The reactant are chosen so that the chemical reaction which results from their mixture causes the contents of the bag to reach from their mixture causes the contents to the bag to reach a preselected temperature and maintain that temperature for some period. Once the thermal bag 7 is specifically manipulated the scrotum is passed through the openings 5 and placed stop the upper drape surface 11 above the thermal bag 7. The adhesive strips 3 are pressed against the penis and body to keep the penis and drape from shifting.

It is also possible to use the instant invention in operations involving body parts other than the scrotum, whenever it is desirable to maintain the surgical field at a predetermined temperature.

Although a particular illustrative embodiment of the present invention has been described herein, the present invention is not limited to this embodiment. Various changes, substitutions and modifications may be made thereto by those skilled in the art without departing from the spirit or scope of the invention defined by the appended claims.

I claim:

1. A temperature-regulating surgical drape for use in conducting surgical procedures on a predetermined body portion of a patient comprising a substantially planar drape body including an opening adapted to expose only said predetermined body portion during said surgical procedure, and means for generating heat affixed to said drape body at a localised predetermined location surrounding at least a portion of said opening for maintaining said predetermined body portion at a predetermined elevated temperature during said surgical procedure.

2. The temperature-regulating surgical drape of claim 1 wherein said opening comprises a circular opening.

3. The temperature-regulating surgical drape of claim 2 wherein said portion of said opening comprises approximately a 180° portion about said circular opening.

4. The temperature-regulating surgical drape of claim 1 wherein said drape body comprises a first layer and a second layer, and wherein said means for generating heat is disposed between said first and second layers.

5. The temperature-regulating surgical drape of claim 1 wherein said means for generating heat comprises a plurality of chemical reactants adapted to maintain said body portion at said predetermined temperature by reacting with each other upon their admixture.

6. The temperature-regulating surgical drape of claim 1 wherein said drape body includes an upper surface and a lower surface, said lower surface including adhesive means located adjacent to said opening for maintaining a body portion other than said predetermined body portion in position below said drape during said surgical procedure.

7. The temperature-regulating surgical drape of claim 6 wherein said adhesive portion comprises a first adhesive portion, wherein said bottom surface of said drape body includes a second adhesive portion for adhesively securing said surgical drape to said body during said surgical procedure.

8. A temperature-regulating surgical drape for use in conducting surgical procedures on the male scrotum comprising a drape body including an opening adapted to expose only said male scrotum while covering the remainder of said body including the penis during said surgical procedure, and means for generating heat affixed to said drape body at a localized predetermined location surrounding at least a portion of said opening so as to be disposed in contact with said male scrotum during said surgical procedure and thereby selectively maintaining said male scrotum at a predetermined elevated temperature during said surgical procedure.

9. The temperature-regulating surgical drape of claim 8 wherein said opening comprises a circular opening.

10. The temperature-regulating surgical drape of claim 9 wherein said means for generating heat is disposed circumferentially around a portion of said circular opening extending approximately 180° about said circular opening.

11. The temperature-regulating surgical drape of claim 8 wherein said drape body comprises a first layer and a second layer, and wherein said means for generating heat is disposed between said first and second layers.

12. The temperature-regulating surgical drape of claim 8 wherein said drape body includes an upper surface and a lower surface, and including adhesive means on said lower surface of said drape body adjacent to said opening so as to maintain said penis in a fixed position during said surgical procedure.

13. The temperature-regulating surgical drape of claim 12 wherein said adhesive means comprises first adhesive means, and including a second adhesive means on said lower surface of said drape for maintaining said surgical drape in position with respect to said body during said surgical procedure.

14. The temperature-regulating surgical drape of claim 8 including activation means for selectively activating said means for generating heat during said surgical procedure.

15. A temperature-regulating surgical drape for use in conducting surgical procedures on a predetermined body portion of a patient comprising a substantially planar drape body including an opening adapted to expose only said predetermined body portion during said surgical procedure, and means for cooling affixed to said drape body at a localized predetermined location surrounding at least a portion of said opening for maintaining said predetermined body portion at a predetermined reduced temperature during said surgical procedure.

16. The temperature-regulating surgical drape of claim 22 wherein said opening comprises a circular opening, and wherein said means for cooling surrounds at least a portion of said opening.

17. The temperature-regulating surgical drape of claim 23 wherein said portion of said opening comprises approximately a 180° portion about said circular opening.

18. The temperature-regulating surgical drape of claim 15 wherein said drape body comprises a first layer and a second layer, and wherein said means for cooling is disposed between said first and second layers.

19. The temperature-regulating surgical drape of claim 15 wherein said means for cooling comprises a plurality of chemical reactants adapted to maintain said body portion at said predetermined reduced temperature by reacting with each other upon their admixture.

20. The temperature-regulating surgical drape of claim 15 wherein said drape body includes an upper surface and a lower surface, said lower surface including adhesive means located adjacent to said opening for maintaining a body portion other than said predetermined body portion in position below said drape during said surgical procedure.

21. The temperature-regulating surgical drape of claim 20 wherein said adhesive portion comprises a first adhesive portion, and wherein said bottom surface of said drape body includes a second adhesive portion for adhesively securing said surgical drape to said body during said surgical portion.

22. A temperature-regulating surgical drape for use in conducting surgical procedure on the male scrotum comprising a drape body including an opening adapted to expose only said male scrotum while covering the remainder of said body including the penis during said surgical procedure, and means for cooling affixed to said drape body at a localized predetermined location surrounding at least a portion of said opening so as to be disposed in contact with said male scrotum during said surgical procedure and thereby selectively maintaining said male scrotum at a predetermined reduced temperature during said surgical procedure.

23. The temperature-regulating surgical drape of claim 22 wherein said opening comprises a circular opening.

24. The temperature-regulating surgical drape of claim 23 wherein said means for cooling is disposed circumferentially around a portion of said circular opening extending approximately 180° about said circular opening.

25. The temperature-regulating surgical drape of claim 22 wherein said drape body comprises a first layer and a second layer, and wherein said means for cooling is disposed between said first and second layers.

26. The temperature-regulating surgical drape of claim 22 wherein said drape body includes an upper surface and a lower surface, and including adhesive means on said lower surface of said drape body adjacent to said opening so as to maintain said penis in a fixed position during said surgical procedure.

27. The temperature-regulating drape of claim 26 wherein said adhesive means comprises first adhesive means, and including a second adhesive means on said lower surface of said drape for maintaining said surgical drape in position with respect to said body during said surgical procedure.

28. The temperature-regulating surgical drape of claim 22 including activation means for selectively activating said means for cooling during said surgical procedure.

* * * * *

UNITED STATES PATENT AND TRADEMARK OFFICE
CERTIFICATE OF CORRECTION

PATENT NO. :    4,807,644

DATED      :    February 28, 1989

INVENTOR(S):    Jeffrey J. Sandhaus

It is certified that error appears in the above-identified patent and that said Letters Patent is hereby corrected as shown below:

```
Column 1, line 13,  delete "surge ion" and insert therefor
                    --surgeon--.
Column 1, line 24,  delete "surge ion" and insert therefor
                    --surgeon--.

Column 5, line 12,  following "portion," insert --and--.
Column 6, line 4,   delete "23" and substitute therefor --16--.
Column 6, line 30,  delete "procedure" and substitute therefor
                    --procedures--.
```

Signed and Sealed this

Twelfth Day of September, 1989

Attest:

DONALD J. QUIGG

Attesting Officer

Commissioner of Patents and Trademarks